United States Patent
Basler

(10) Patent No.: US 6,702,649 B2
(45) Date of Patent: Mar. 9, 2004

(54) METHOD OF DETERMINING CURRENT POSITION DATA OF A MACHINING TOOL AND APPARATUS THEREFOR

(75) Inventor: Franz Basler, Ketsch (DE)

(73) Assignee: Sirona Dental Systems GmbH, Bensheim (DE)

( * ) Notice: Subject to any disclaimer, the term of this patent is extended or adjusted under 35 U.S.C. 154(b) by 137 days.

(21) Appl. No.: 10/059,058

(22) Filed: Jan. 30, 2002

(65) Prior Publication Data

US 2002/0102915 A1 Aug. 1, 2002

(30) Foreign Application Priority Data

Jan. 30, 2001 (DE) .......................... 101 04 287

(51) Int. Cl.⁷ .......................... B24B 49/00; B24B 51/00
(52) U.S. Cl. .................. 451/9; 451/8; 451/10; 451/11; 451/246; 451/913
(58) Field of Search .............. 451/5, 8, 9, 10, 451/11, 49, 50, 246, 913; 29/407.01; 408/3; 409/2, 79, 289

(56) References Cited

U.S. PATENT DOCUMENTS

| | | | |
|---|---|---|---|
| 4,461,125 A | * | 7/1984 | Wuest .............................. 451/5 |
| 4,934,105 A | * | 6/1990 | Sigg ............................... 451/5 |
| 6,361,410 B1 | * | 3/2002 | Sakai et al. .................... 451/56 |
| 6,394,880 B1 | * | 5/2002 | Basler et al. .................. 451/28 |
| 6,411,861 B1 | * | 6/2002 | Clewes et al. .............. 700/164 |
| 6,454,629 B1 | * | 9/2002 | Basler et al. .................... 451/5 |

FOREIGN PATENT DOCUMENTS

DE 40 30 175 C2 4/1997

* cited by examiner

*Primary Examiner*—Timothy V. Eley
(74) *Attorney, Agent, or Firm*—Dykema Gossett PLLC

(57) ABSTRACT

The current positioning data of a machining tool with regard to a reference surface of a workpiece or of a body connected to the workpiece, is determined. The tool and the workpiece to be machined are relatively moveable toward and away from one another, and the rotary speed of a drive motor for the tool is set to a starting rotary speed which is so low that, when the tool comes into contact with the reference surface, its rotary speed is measurably reduced, the reference surface is moved past the tool before the tool is in contact and while the tool is in contact. As a result, the braking moments in the bearings are increased, and the drive motor comes to a stop quicker.

15 Claims, 2 Drawing Sheets

METHOD OF DETERMINING CURRENT POSITION DATA OF A MACHINING TOOL AND APPARATUS THEREFOR

RELATED APPLICATIONS

This application relates to application Ser. No. 09/596,082, filed Jun. 16, 2000, now U.S. Pat. No. 6,394,880, and to application Ser. No. 10/058,996, filed Jan. 30, 2002, entitled Method of Determining Current Position Data of A Machining Tool and Apparatus Therefor, of Bernd Rothenberger, both applications commonly owned herewith. The entirety of the disclosures of both applications are specifically incorporated herein by reference.

TECHNICAL FIELD

The invention relates to a method of determining current positioning data of a machining tool and to an apparatus for this purpose and is to be used in particular in the production of ready-to-use tooth-restoration fitting bodies by means of grinding instruments in dental CAD/CAM grinding machines.

PRIOR ART

Grinding pencils having a surface of defined shape are especially suitable for the form-grinding of ceramic blanks. In an automated production process, it is necessary in this case to measure the position and dimension of the grinding pencil before each operation, but at least after changing the grinding pencil. This measuring can be achieved by feeling for a workpiece of known size. The feeling operation essentially comprises a grinding pencil rotating at low speed and a movement of the grinding pencil toward the workpiece or a movement of the workpiece toward the grinding pencil. The feeling operation is ended by the frictional contact between workpiece and grinding pencil, if the frictional contact has reduced the rotary speed of the grinding pencil to zero.

DE 40 30 175 C2 discloses a method of calibrating a motor-driven tool, which can be moved by means of a feed device toward and away from a workpiece to be machined, with regard to the workpiece or a holder accommodating the workpiece, and an apparatus for carrying out the method.

It has been found that the method described there reaches its limits when the shape of the frictional surfaces becomes extremely undefined or small, which, in particular in the case of grinding pencils narrowing toward the tip, can lead to considerable positioning inaccuracies during the axial feeling with the tip.

The object of the invention is to determine the exact linear positioning data of a tool having any desired tip geometry.

SUMMARY OF THE INVENTION

The machining tool according to the invention is moved in a slowly rotating manner toward a workpiece slowly rotating perpendicularly to the feed direction and having known geometry. If the tool strikes the workpiece, the rotation of the tool is stopped by the frictional load between workpiece and tool. In addition to the frictional load, a tangential force acts on the tip of the machining tool on account of the workpiece rotation, and this tangential force leads to increased frictional forces in the bearing arrangement of the drive shaft of the tool, so that the position in the feed direction can be determined in a considerably more precise manner.

It has been found that the penetration depth and in particular the variance of the penetration depth of the tool in the workpiece until the drive braked by the frictional forces comes to a stop can be markedly reduced in the case of certain tip geometries, which is immediately reflected in the accuracy of the determination of the position.

Advantageous developments are specified in the subclaims.

In addition, the present invention includes an apparatus for carrying out the method according to the invention.

In the case of the apparatus, there is a feed device with which the tool can be moved toward and away from a workpiece. Furthermore, the apparatus contains a first spindle for accommodating the workpiece, at least one further spindle for accommodating in each case at least one machining tool which can be set in rotation and has an end machining surface, the spindles being arranged and mounted in such a way that the machining tool and workpiece can be moved toward and away from one another for the purpose of material removal at the workpiece. Furthermore, the apparatus also contains drive motors for adjusting the spindles and for the drive of the machining tool and at least one reference surface which is arranged on the workpiece, on the work holder or on the clamping device and against which the end machining surface of the machining tool travels, a signal establishing the feed path of the tool being produced upon contact with the reference surface, which signal is used for determining the starting position of the machining tool. In addition, drive means are provided for moving the reference surface along the end machining surface of the machining tool during the contact produced by the feed, and a contact surface is formed with the reference surface by the end machining surface of the tool, the contact surface being asymmetrical and having direction components both in the feed direction and in the direction radial thereto, although only over a part of the circumference.

Advantageously, the tool has a narrowing tip and is in this case designed in particular as a spherical grinding pencil or tapered grinding pencil with tip.

BRIEF DESCRIPTION OF THE DRAWING

An exemplary embodiment of the invention is shown in the drawing, in which.

DETAILED DESCRIPTION OF THE INVENTION

Figure 1:
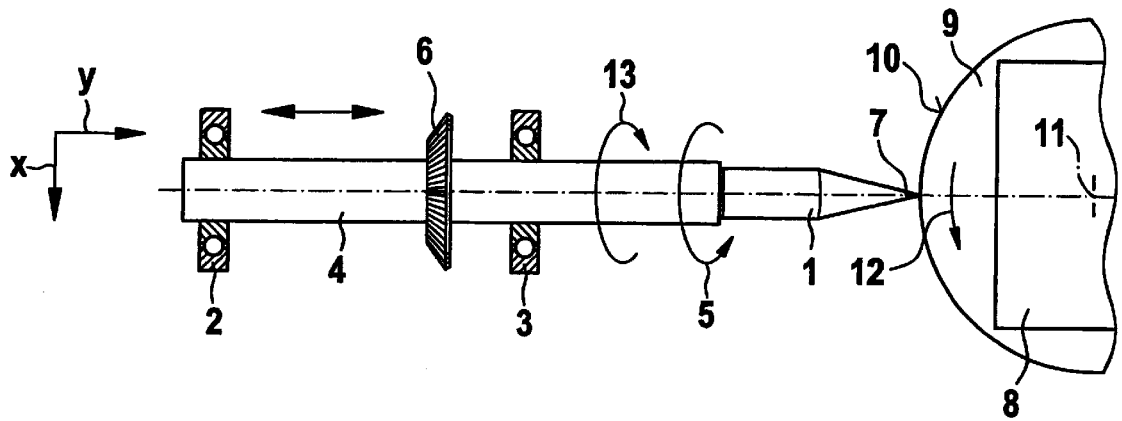
FIG. 1 shows a diagrammatic sketch of a machining tool with a drive shaft during the contact operation at a tool.

The diagrammatic sketch shown in FIG. 1 shows a machining tool 1 in the form of a tapered grinding pencil, which is set in rotation according to arrow 5 via a drive shaft 4 mounted in a housing (not shown) by means of a first bearing 2 and a second bearing 3. To this end, the drive shaft 4 is connected to a gear 6 which is arranged between the first bearing 2 and the second bearing 3 and on which a drive motor (not shown) acts.

A workpiece 8, which is fastened to a holder 9 having a reference surface 10, is arranged at a distance from a tip 7 of the machining tool. The reference surface 10 together with the holder 9 and the workpiece 8 can be moved about a rotation axis 11 in the direction of the arrow 12 past the tip 7.

Via means which are not shown, the entire drive shaft 4 and thus also the tool 1 can be moved toward and away from the workpiece 8 to be machined as shown in the direction of the double arrow.

To determine the current positioning data of the machining tool 1 with regard to the workpiece 8 or the holder 9 accommodating the workpiece 8, the holder 9, in the exemplary embodiment, has the reference surface 10, with which the tool, with its tip, is brought into contact.

The rotary speed of the drive motor for the tool 1 is set to a starting rotary speed which is so low that, when the tool tip 7 comes into contact with the reference surface 10, the rotary speed of the drive motor becomes zero due to the frictional forces caused by this. The drive motor is thus braked on account of friction until it comes to a stop.

To assist the formation of frictional forces at a tip 7 tapering to a point, the workpiece 8 or the holder 9 accommodating the workpiece 8 is already moved past the tool tip 7 before and even during the contact with the tool tip 7, this contact being effected by the feed. Drive means (not shown) are provided for this purpose.

By just the contact, caused solely by the feed of the tool 1, between the tip 7 and the reference surface 10, a braking moment, opposed to the drive moment 5, in the direction of arrow 13 is produced on account of the friction and as a rule on account of material removal at the reference surface by the tip itself. It is immediately clear that this braking force in the case of a conically tapering tip has to remain very small at the start on account of the virtually point-like contact area, so that a sufficiently large braking moment is built up only during further feed of the tool tip and during correspondingly deep penetration into the reference surface.

In addition to the contact produced by the feed and the braking moment resulting therefrom, a further braking moment is built up in the bearings of the drive shaft by the transverse force resulting from the movement of the reference surface along the tip, as a result of which the drive shaft comes to a stop much sooner than without a movement of the reference surface.

Figure 2:
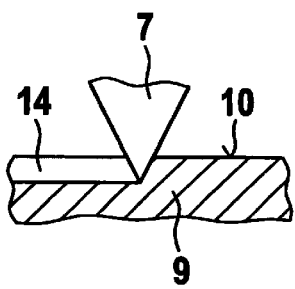
FIG. 2 shows a cross-sectional detail view of a tool tip plunged into a reference surface.

A detail view of a tool tip 7 plunged into a reference surface 10 is shown in cross section in FIG. 2. It can be seen here that a groove 14 has formed due to the plunging of the tool tip and the movement of the reference surface 10 past the tool tip 7.

Figure 3:
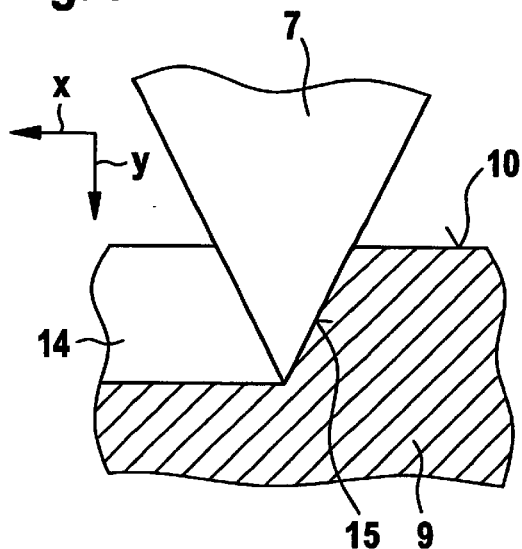
FIG. 3 shows an enlargement of FIG. 2 for illustrating the asymmetric contact surface of the tool with the reference surface.

It can be seen in FIG. 3 that the tool tip 7 has a surface 15 in contact with the holder 9, this contact surface 15 being asymmetrical given the formation of the groove 14 formed, and having both axial and radial direction components (y-direction and x-direction).

Figure 4:
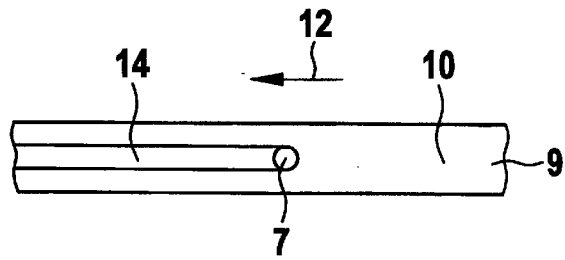
FIG. 4 shows a plan view of the reference surface with a plunged tool tip.

A plan view of the reference surface 10 with a plunged tool tip 7 is shown in FIG. 4, this plan view clearly showing the movement, represented by the arrow 12, of the reference surface 10 past the tool tip 7. In this case, the reference surface 10 has been developed in a plane. On account of the tool tip 7 plunged into the reference surface 10, the groove 14 has been produced before the braking moments have braked the drive motor.

When the drive motor is braked, care is taken to ensure that the reference surface 10 cannot continue to rotate. This is done by the rotary speed of the machining tool or of the drive motor being used as a command variable for the movement of the reference surface. If the rotary speed of the tool drops, the movement of the reference surface is reduced. If the tool is braked down to 0, the movement of the reference surface also becomes 0. In addition, it is possible also to couple the feed of the tool with the rotary speed of the tool by the feed of the tool toward the reference surface also being reduced when the rotary speed of the tool is reduced. If the rotation of the machining tool is equal to zero on account of the friction which occurs, the feed of the machining tool is also no longer effected.

In addition, a preloaded spring element may be provided in a feed device of the drive shaft or at the drive shaft itself, this spring element, by spring deflection under load, absorbing the forces acting on the stationary tool. In the process, the spring deflection is preferably effected against the direction of the feed, the preloading of the spring element having to be selected to be large enough in order to exceed the envisaged loads on the tool which occur as planned during the machining. Spring deflection therefore takes place only for protecting the tool against overload. As a result, damage to the tool tip caused by overload can be avoided on the one hand, and accurate machining of the workpiece with the tool tip can be effected on the other hand.

Figure 5:
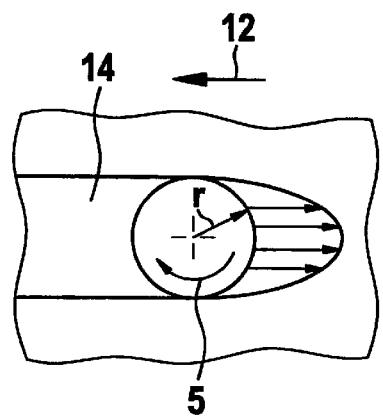
FIG. 5 shows an enlargement of the tool tip from FIG. 4 with an assumed radial force profile on the tool.

An enlargement of the tool tip 7 from FIG. 4 with an assumed radial force profile at the tool tip 7 is shown in FIG. 5. For each radial force, a frictional force opposed to the direction of rotation according to arrow 5 is produced, and this frictional force bears tangentially against the lateral surface of the tip 7 and, on the one hand, produces a braking moment having the lever arm r and, on the other hand, generates bearing forces at the drive shaft due to the asymmetrical distribution.

During the movement of the tool toward the workpiece, the reference surface of the workpiece covers a path which is at most ten times the desired accuracy of the machining, preferably less than 0.2 mm.

This is intended to ensure that eccentricity of the reference surface, which has been determined in another way and is known, does not impair the accuracy of the position detection of the tool tip. In the case of a cylindrical reference surface, small deviations during the alignment of the tool with the center axis of the reference surface only have a slight effect. Nonetheless, the position of the center axis of a cylindrical reference surface should have been accurately determined beforehand and contact should be effected with a feed direction aligned with the center axis.

It has been found that, when determining the position of a diamond grinding pencil at an aluminum reference surface, it is sufficient if the machining tool, before contact, being driven at a rotary speed of less than one hundredth of the rotary speed used for the machining, in particular at 1 to 10 revolutions/second.

The tool 1 and the reference surface 10 are oriented with respect to one another before the actual contact for determining the position of the tool tip 7, this involving a rough determination of the position with regard to the distance from the reference surface 10. A slow infeed of the tool toward the reference surface does not take place until after this rough determination of the position, which may be effected with markedly greater feed rates compared with the subsequent determination of the position, so that a shorter time is required overall.

The machining tool 1, with respect to the feed axis, is oriented in alignment with a rotary center 11 of a cylindrical reference surface 10. If the exact position of the rotary center of the reference surface is still not known at this instant, it can be determined by infeed of the tool in the feed direction until it comes into contact with the reference surface 10. The absolute distance of the tool from the rotary center can then be determined from the known diameter of the reference surface. In order to take eccentricity into account, it may be necessary to make further contact at a reference surface preferably rotated by 180°.

Before the actual determination of the position, the plane containing the rotary center 11 of the reference surface 10 and extending in or parallel to the feed direction and the eccentricity of the reference surface 10 are established. To this end, the machining tool 1 can be brought laterally up to the reference surface. At least two locations must be approached laterally in order to be able to set up the circle equation using the diameter of the reference surface. Further locations permit statements about the eccentricity in various directions.

Before the actual determination of the position of the tool 1 with regard to the reference surface 10, one or more feeling operations with stationary reference surface 10 may be effected.

After the determination of the position, the established position can be changed by a predetermined correction value, for example in order to take into account inertia-related system properties. As a result, the accuracy can be improved again.

Figure 6:
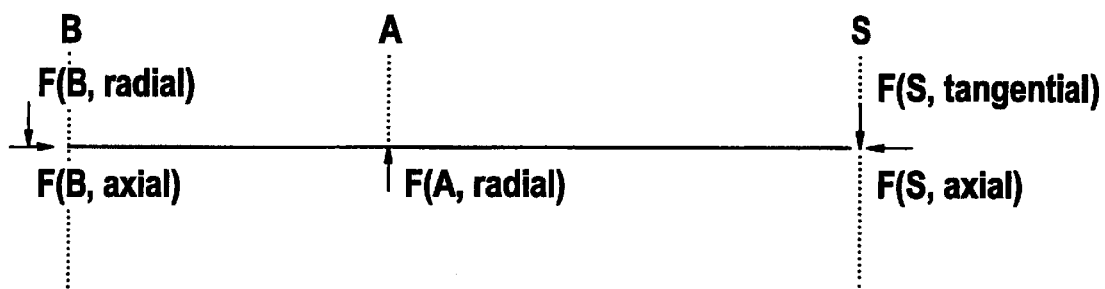
FIG. 6 shows a hypothetical force profile.
Figure 7:
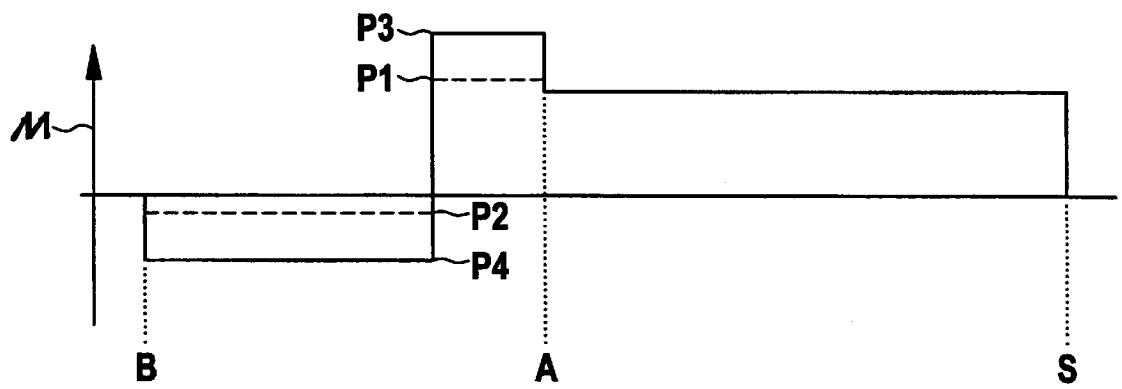
FIG. 7 shows a hypothetical moment profile.

A hypothetical force profile is shown in FIG. 6 and a hypothetical moment profile is shown in FIG. 7, using a grinding pencil having a tapered tip as an example. Before each grinding operation, the grinding pencil is positioned axially relative to the rotary center of a cylindrical workpiece. Care is taken to ensure that the distance between the tip of the grinding pencil and the workpiece is very short, so that only short feeling paths are to be covered and the effect of the eccentricity of the workpiece, which becomes apparent during the rotation of the workpiece, becomes negligibly small. This may be done by a preceding rough feeling operation with stationary workpiece.

The grinding pencil is then set in slow rotation (1–10 Hz). In the process, just so much power is fed to the drive motor, which engages in the drive shaft 4 with a gear 6, that the friction moments of the actual bearing arrangement and of the gear grease are overcome. At the same time, the rotary speed of the grinding pencil is set so low that initial damage to the grinding pencil can be ruled out.

The workpiece is now set in slow rotation and the grinding pencil is moved in the axial direction toward the workpiece. In the process, the rotary speed of the workpiece is selected to be very small, so that the tip of the grinding pencil sweeps only a small part of the circumference of the workpiece on the feed path. The effect of the eccentricity of the workpiece thus becomes negligible.

When the grinding pencil comes into contact with the workpiece, the diamond tip of the grinding pencil produces a friction moment between diamond and workpiece surface, and this friction moment counteracts the rotation of the grinding pencil. The stoppage of the grinding pencil can then be detected via sensors on the motor shaft, and the current feed position can be stored.

In addition to the force F (S, axial) which is caused by the grinding pencil by means of friction, acts in the axial direction and introduces a small braking moment to the shaft, a tangential force F (S, tangential) caused by the rotation of the reference surface also acts. This additionally results in forces in the bearings A and B or 2 and 3 from FIG. 1. The following situation arises:

$$F_{(B, axial)} - F_{(S, axial)} = 0$$

$$F_{(B, radial)} - F_{(A, radial)} + F_{(S, tangential)} = 0$$

For the resulting moment:

$$F_{(B, radial)} * \text{distance } (B, A) = F_{(S, tangential)} * \text{distance } (A, S)$$

This results in the additional radial force components in the bearings A, B:

$$F_{(B, radial)} = F_{(S, tangential)} * (\text{distance } (A, S)/\text{distance } (B, A))$$

$$F_{(A, radial)} = F_{(S, tangential)} * (1 + \text{distance } (A, S)/\text{distance } (B, A))$$

These radial force components produce, via the coefficient of friction, an additional braking moment on the gear 5 (depicted in FIG. 1) and the drive motor.

In the sketched moment profile according to FIG. 7, the difference in the moment of the points P1–P2 corresponds to the generated braking moment without workpiece rotation, and the difference P3–P4 corresponds to the generated braking moment with workpiece rotation, that is to say with tangential force F (S, tangential).

What is claimed is:

1. A method of determining current position data of a machining tool during machining with regard to a reference surface of a workpiece or a body connected to the workpiece, comprising the steps of:

relatively moving the tool and the workpiece toward and away from one another along a feed axis;

providing a drive motor for the tool and setting the rotary speed of the drive motor to a starting rotary speed which is so low that when bringing the tool into contact with the reference surface, the rotary speed is measurably reduced;

wherein the reference surface is moved past the tool before the tool is in contact and while the tool is in contact.

2. The method as claimed in claim 1, wherein during the movement of the tool toward the workpiece, the reference surface covers a path which is at most ten times the desired accuracy of the machining.

3. The method as claimed in claim 1, wherein the machining tool, before the contact, is driven at a rotary speed of less than one hundredth of the rotary speed used for the machining, in particular at a rotary speed of 1 to 10 revolutions/second.

4. The method as claimed in claim 1, wherein the tool and the reference surface are oriented with respect to one another before actual determination of the position data.

5. The method as claimed in claim 4, wherein before actual determination of position data of the tool with regard to the reference surface, at least one feeling operation with a stationary reference surface is effected.

6. The method as claimed in claim 1, wherein the machining tool, with regard to the feed axis, is oriented in alignment with a rotary center of the reference surface which is cylindrical.

7. The method as claimed in claim 6, wherein before actual determination of position data, the plane containing the rotary center of the reference surface and extending in or parallel to the feed direction and the eccentricity of the reference surface are established.

8. The method as claimed in claim 1, wherein the movement of the reference surface is coupled with the rotary speed of the drive motor for the tool in such a way that a reduction in the rotary speed of the drive motor brings about a reduction in the movement of the reference surface.

9. The method as claimed in claim 8, wherein the movement of the reference surface or of the feed of the tool is stopped if the rotary speed of the drive motor of the tool becomes zero.

10. The method as claimed in claim 1, wherein the feed of the tool is coupled with the rotary speed of the drive motor for the tool in such a way that a reduction in the rotary speed of the drive motor brings about a reduction in the feed of the tool.

11. The method as claimed in claim 1, wherein during a feeling operation of a tip of the tool relative to the reference surface, so much power is fed to the drive motor that the friction moments of the actual bearing arrangement and of all the lubrication thereof are just overcome.

12. The method as claimed in claim 1, wherein the established position is changed by a predetermined correction value.

13. An apparatus for determining current position data of a machining tool, comprising a feed device to effect relative movement of the tool and a workpiece toward and away from one another, a first spindle for accommodating the workpiece, at least one further spindle for accommodating the machining tool which can be set in rotation and has an end machining surface, the spindles being arranged and mounted in such a way that the machining tool and workpiece can be moved relatively toward and away from one another for the purpose of material removal at the workpiece, drive motors for adjusting the spindles and for the drive of the machining tool, at least one reference surface which is arranged on one of the workpiece, a work holder and a body connected to the workpiece and against which the end machining surface of the machining tool travels, a signal establishing the feed path of the tool being produced upon contact with the reference surface, which signal is used for determining the starting position of the machining tool, drive means being provided for moving the reference surface along the end machining surface of the machining tool during the contact produced by the feed, and a contact surface being formed with the reference surface by the end machining surface of the tool, the contact surface being asymmetrical and having direction components both in the feed direction and in the direction radial thereto, although only over a part of the circumference of the workpiece.

14. The apparatus as claimed in claim 13, wherein the tool has a narrowing tip and comprises a tapered grinding pencil with tip.

15. The apparatus as claimed in claim 13, wherein the drive means for moving the reference surface is coupled with the rotary speed of the machining tool in such a manner that a reduction in the rotary speed of the machining tool reduces the movement brought about by the drive means.

* * * * *